(12) United States Patent
Candy

(10) Patent No.: US 6,490,469 B2
(45) Date of Patent: Dec. 3, 2002

(54) METHOD AND APPARATUS FOR DYNAMIC FOCUSING OF ULTRASOUND ENERGY

(75) Inventor: James V. Candy, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 64 days.

(21) Appl. No.: 09/809,961

(22) Filed: Mar. 14, 2001

(65) Prior Publication Data

US 2001/0037075 A1 Nov. 1, 2001

Related U.S. Application Data

(60) Provisional application No. 60/189,382, filed on Mar. 15, 2000.

(51) Int. Cl.[7] .................................................. A61B 5/00
(52) U.S. Cl. ....................... 600/407; 600/439; 600/443; 601/2; 73/602
(58) Field of Search ................................ 600/487–492, 600/407–436; 601/2

(56) References Cited

U.S. PATENT DOCUMENTS

| | | | |
|---|---|---|---|
| 4,848,356 A | | 7/1989 | Nakamura et al. |
| 4,873,869 A | * | 10/1989 | Fink ............................ 600/443 |
| 4,938,225 A | * | 7/1990 | Fink ............................ 600/437 |
| 4,995,397 A | | 2/1991 | Nishiyama et al. |
| 5,010,885 A | * | 4/1991 | Fink et al. ................... 600/442 |
| 5,092,336 A | * | 3/1992 | Fink ............................ 600/447 |
| 5,163,434 A | | 11/1992 | Kumazawa |
| 5,276,654 A | * | 1/1994 | Mallart et al. ............... 600/443 |
| 5,331,964 A | | 7/1994 | Trahey et al. ........... 128/661.01 |
| 5,394,151 A | | 2/1995 | Knaell ........................... 342/25 |
| 5,428,999 A | * | 7/1995 | Fink ............................ 367/103 |
| 5,431,053 A | * | 7/1995 | Fink .............................. 73/598 |
| 5,632,277 A | | 5/1997 | Chapman et al. |
| 5,673,699 A | * | 10/1997 | Trahey et al. ................. 73/596 |
| 5,675,554 A | | 10/1997 | Cole et al. |
| 5,706,819 A | | 1/1998 | Hwang et al. |
| 5,827,188 A | | 10/1998 | Wright et al. |
| 5,876,341 A | | 3/1999 | Wang et al. |
| 5,935,068 A | | 8/1999 | Zhu et al. ..................... 600/443 |
| 5,951,478 A | | 9/1999 | Hwang et al. |
| 5,980,459 A | | 11/1999 | Chiao et al. |

FOREIGN PATENT DOCUMENTS

| | | | | |
|---|---|---|---|---|
| EP | 0916967 A2 | 5/1999 | | G01S/7/52 |
| EP | 0952461 A2 | 10/1999 | | G01S/15/89 |

OTHER PUBLICATIONS

M. Fink, C. pRada, F. Wu, D. Cassereau, Self Focusing Inhomogeneous Media With "Time Reversal" Acoustic Mirrors, IEEE Ultrasonics Symposium, 1989, pp. 681–686.*

(List continued on next page.)

*Primary Examiner*—Francis J. Jaworski
*Assistant Examiner*—William Jung
(74) *Attorney, Agent, or Firm*—Eddie E. Scott; Christopher J. Horgan; Alan H. Thompson

(57) ABSTRACT

Method and system disclosed herein include noninvasively detecting, separating and destroying multiple masses (tumors, cysts, etc.) through a plurality of iterations from tissue (e.g., breast tissue). The method and system may open new frontiers with the implication of noninvasive treatment of masses in the biomedical area along with the expanding technology of acoustic surgery.

20 Claims, 5 Drawing Sheets

OTHER PUBLICATIONS

M. Fink, Time Reversal of Ultrasonic Fields–Part I: Basic Principle, IEEE Trans On Ultrasonics, Ferroelectrics, and Frequency Control, vol. 39, No. 5, Sep. 1992, pp. 555–566.*

James V. Candy, "Time–reversal signal processing: Background, theory, and application," Journal of the Acoustical Society of America, vol. 101, No. 5, pt. 2, May 1997, p. 3089 XP002176056.

M. Fink, et al., "Aberration Correction in Ultrasonic Medical Imaging with Time–Reversal Techniques," Int. J. Imaging Systems & Technology, 8 (1997), pp. 110–125.

M. Fink, "Time Reversal in Acoustics," Contemporary Physics, 1996, vol. 137, No. 2, pp. 95–109.

M. Fink, "Time Reversal of Ultrasonic Fields—Part I: Basic Principles," IEEE Trans. On Ultrasonics, Ferroelectrics, and Frequency Control, vol. 39, No. 5, Sep. 1992, pp. 555–565.

F. Wu, et al., "Time Reversal of Ultrasonic Field—Part II: Experimental Results," IEEE Trans. On Ultrasonics, Ferroelectrics, vol. 39, No. 5, Sep. 1992, pp. 567–578.

M. Fink, "Time Reversed Acoustics," Physics Today, Mar. 1997, pp. 34–40.

J.L. Thomas, et al., "Ultrasonic Beam Focusing Through Tissue Inhomogeneities with a Time Reversal Mirror: Application to Transskull Therapy," IEEE Trans. On Ultrasonics, Ferroelectrics, vol. 43, No. 6, Nov. 1996, pp. 1122–1129.

C. Dorme, et al., "Ultrasonic Beam Steering Through Inhomogeneous Layers with a Time Reversal Mirror," IEEE Trans. On Ultrasonics, Ferroelectrics, vol. 43, No. 1, Jan. 1996, pp. 167–175.

* cited by examiner

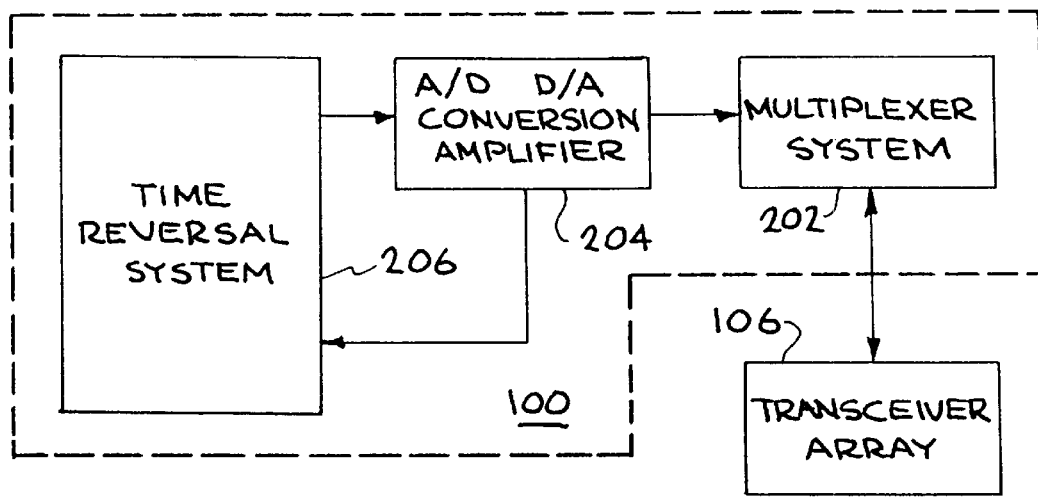
FIG. 2A
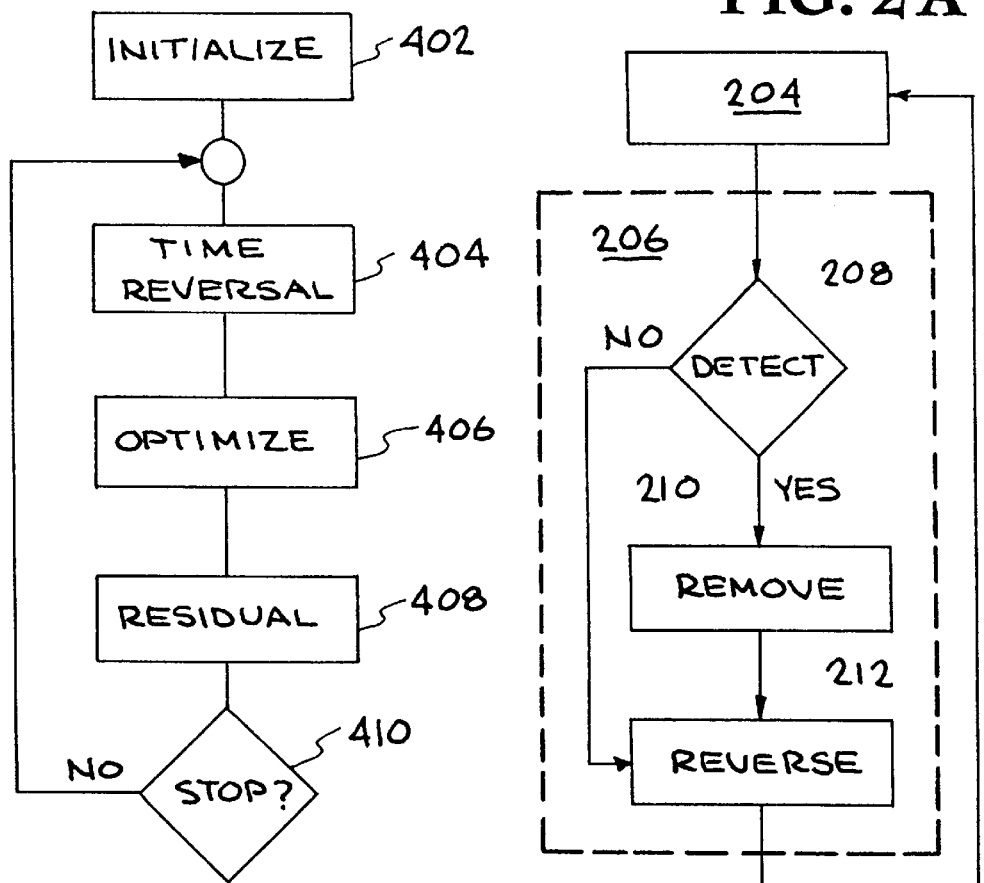
FIG. 4
FIG. 2B

METHOD AND APPARATUS FOR DYNAMIC FOCUSING OF ULTRASOUND ENERGY

RELATED APPLICATION

This application relates to U.S. Provisional Application No. 60/189,382 filed Mar. 15, 2000, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The ability to detect an acoustic source(s) or target(s) or multiple scatterers covers a broad spectrum of applications ranging from the detection and destruction of painful kidney or gall stones in biomedical, to active target detection in underwater acoustics, to the detection of flaws/cracks in a critical part during nondestructive evaluation (NDE). These applications have at least one common element—they are based on a pulse-echo principle for detection. The applications are usually concerned with detection, imaging and sometimes destruction (biomedical) of the reflective source or in new techniques for acoustic surgery. In these types of systems, a piezoelectric transducer (PZT) may first transmit a short transient pulse and then detect the echoes received back from the various scatterers.

SUMMARY OF THE INVENTION

An aspect of the invention includes a method of decomposing a plurality of scatterers in a medium in the time domain comprising: a) transmitting a time reversed field into the plurality of scatterers of the medium and performing a sequence of time-reversal iterations to extract contribution of the i-th scatterer of the plurality of scatterers;

b) estimating a weighting coefficient of the i-th scatterer of the plurality of scatterers;

c) estimating the plurality of scatterers of the medium with the i-th scatterer removed;

d) testing to see if a decomposition condition is satisfied; and e) performing a plurality of iterations of steps a through d until the decomposition condition is satisfied.

A further aspect of the invention may include an array capable of transmitting an acoustic wave; and a storage and reversal circuit operatively coupled to the array and designed to receive time series measurement data of a plurality of scatterers in a medium and decompose the plurality of scatterers by systematically focusing on each of the plurality of scatterers and sequentially removing from the time series measurement data the plurality of scatterers.

BRIEF DESCRIPTION OF THE DRAWINGS

The accompanying drawings, which are incorporated into and form a part of the disclosure.

FIGS. 2A–2B illustrate a block diagram of a storage and reversal unit;

FIG. 4 illustrates a flow diagram of an iterative time-reversal dynamic focusing operation.

DETAILED DESCRIPTION OF THE INVENTION

When a wave propagates through a spatio-temporal medium (e.g., tissue), the resulting wavefront is distorted. This distortion is related to the medium as well as the type of source creating this phenomenon. If a media is homogenous, then its sound velocity profile, density/temperature profile, index of refraction or related velocity function is independent of spatial position. An inhomogenous medium possesses an inherent property related to velocity that does vary with spatial position. If the medium is homogenous and the source resides in the near-field, then a spherical-type wavefront evolves. But if the medium is inhomogenous, then a distorted wavefront results. In the homogenous medium, simple time-delay processing is sufficient to enhance the field at a given point; however, this is not necessarily the case in an inhomogenous medium, since the amplitude as well as the phase may be distorted during propagation. The use of time delay estimation and even adaptive time delay estimation techniques become quite limited and unsuccessful in an inhomogenous medium excited by a broadband incident field requiring an alternative approach to solve the field reconstruction and focusing problem.

Disclosed herein is a method and system for dynamic focusing of ultrasonic energy to address the inhomogenous field reconstruction and focusing problem to both detect, separate and destroy selected masses (e.g., tumors, cysts, etc.) in inhomogenous mediums such as breasts and other parts of the anatomy. These selected masses may be referred to as scatterers, sources (i.e., sources of reflected waves) or flaws. A methodology is disclosed herein to obtain time series measurement data (or "data") reconstructing the inhomogenous medium using time-reversal (T/R) focusing. Typical time-reversal focusing techniques may involve focusing on the strongest scatterer and destroying it. Time-reversal focusing is used in the disclosed dynamic focusing technique to iteratively "remove" from the time series measurement data the aberrations created by an inhomogeneous medium illuminated by propagating waves. This technique may be used to iteratively and sequentially "focus" on the principal scatterer or flaw dominating a pulse-echo response. Once detected that particular scatterer may be removed from the time series measurement data to allow for the focus on the next strongest scatterer. This process may be repeated until substantially all of the scatterers have been detected and removed from the time series measurement data. The applicability of time-reversal processing to focus energy without the need to model the medium is an advantageous property, since most media are unknown and random and temporal coherence or time delay processing no longer is applicable.

Figure 1A:
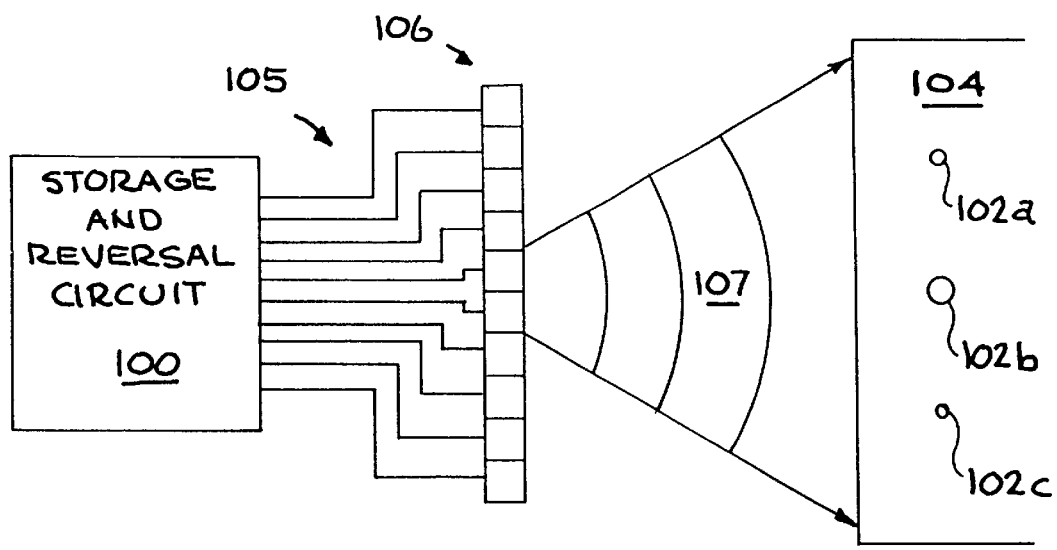
FIGS. 1A–1F are schematic diagrams of an iterative time-reversal dynamic focusing operation.

Hardware which may be used in a time reversal system is illustrated in FIGS. 1A–1F. FIG. 1A discloses a storage and reversal circuit 100 coupled through multiple connections 105 (e.g., wires) to an array 106 made up of a plurality of programmable ultrasonic transceiver elements 1, 2, . . . n. Although the transceiver elements are shown in a one-dimensional array 106, they may also be organized into a two-dimensional array. The transceiver elements may be piezo-electric devices. Reference numeral 104 indicates an inhomogenous medium which contains a plurality of scatterers 102$a$, 102$b$, and 102$c$ of varying sizes. Although only three scatterers 102$a$, 102$b$, and 102$c$ are shown, the time reversal system disclosed herein may work on a far greater number.

Figure 1B:
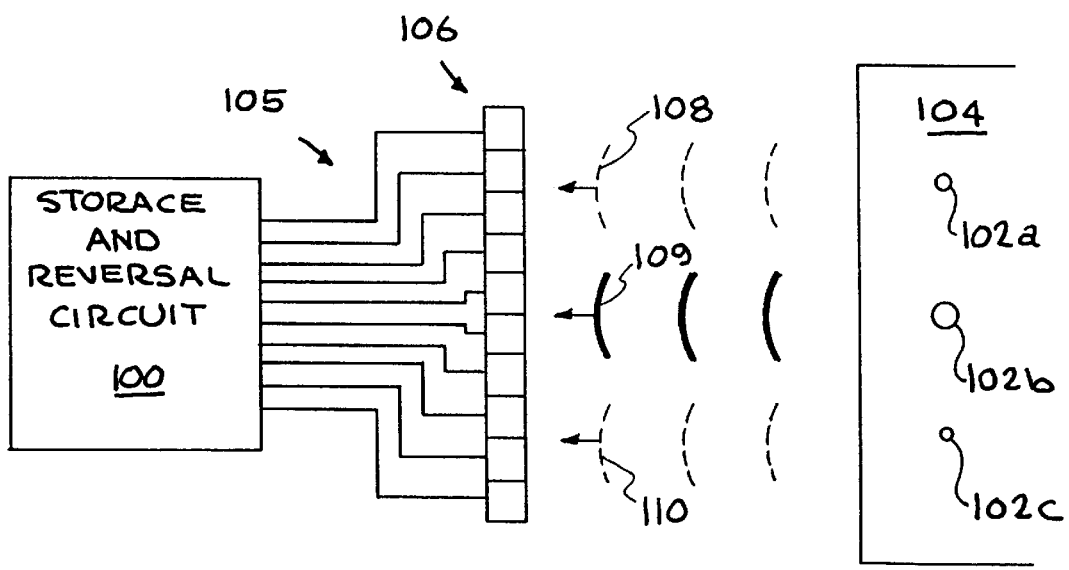
Figure 1C:
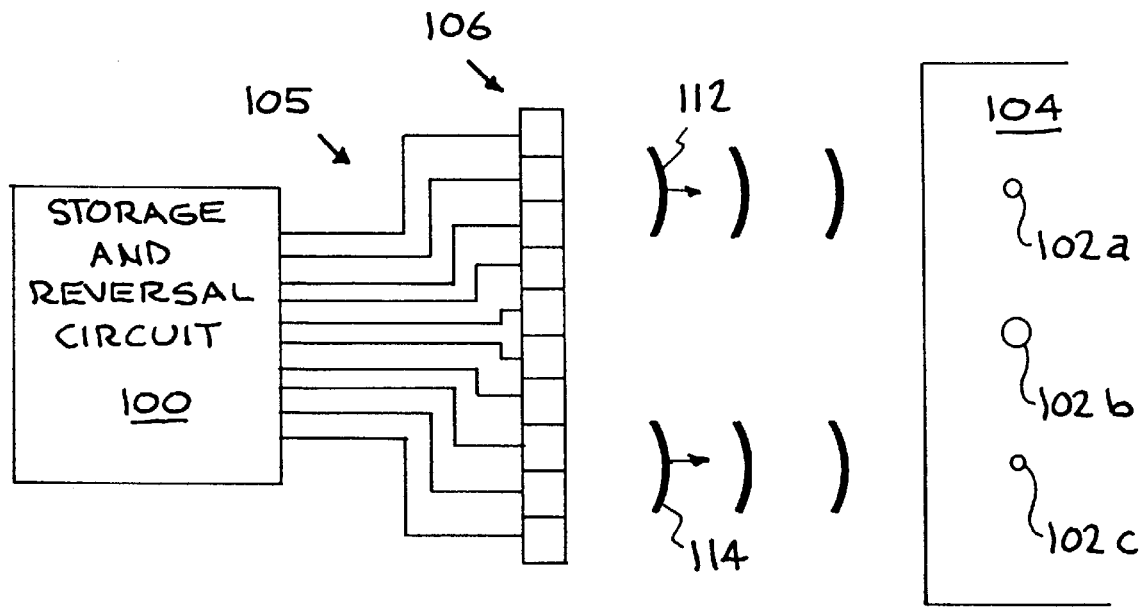
Figure 1D:
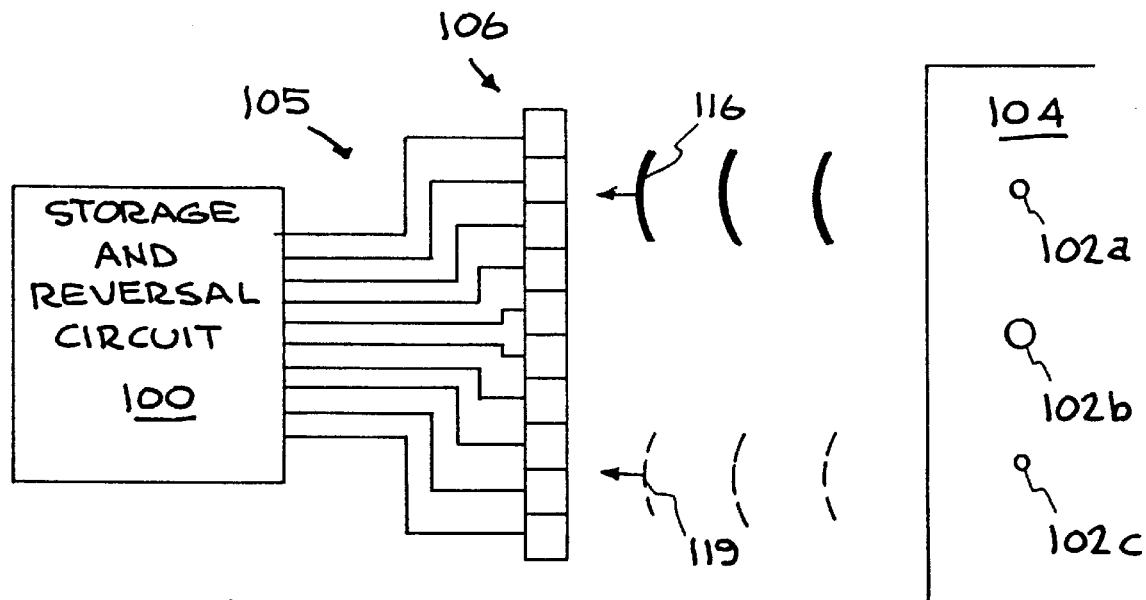
Figure 1E:
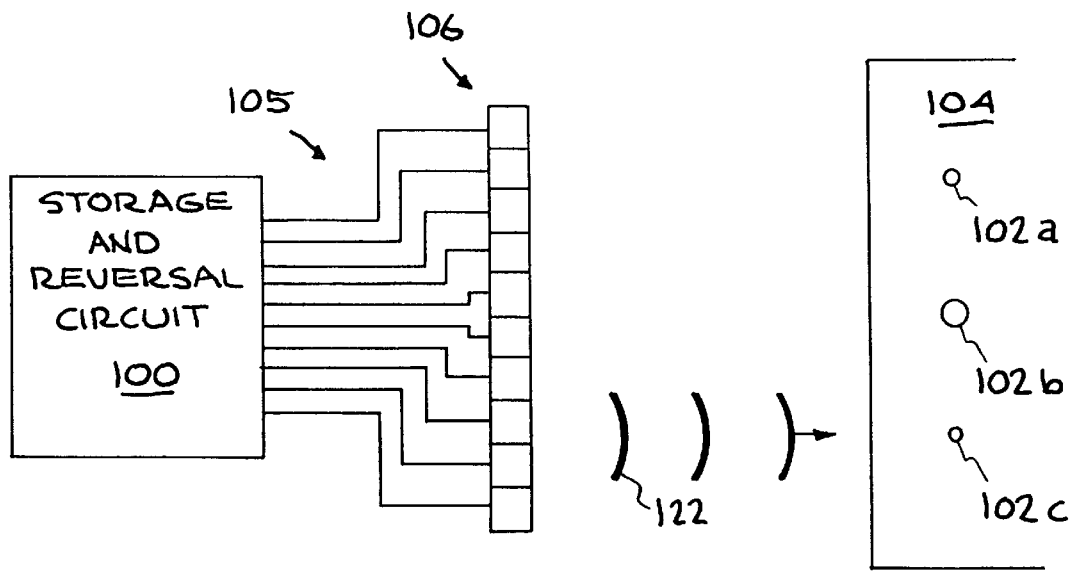
Figure 1F:
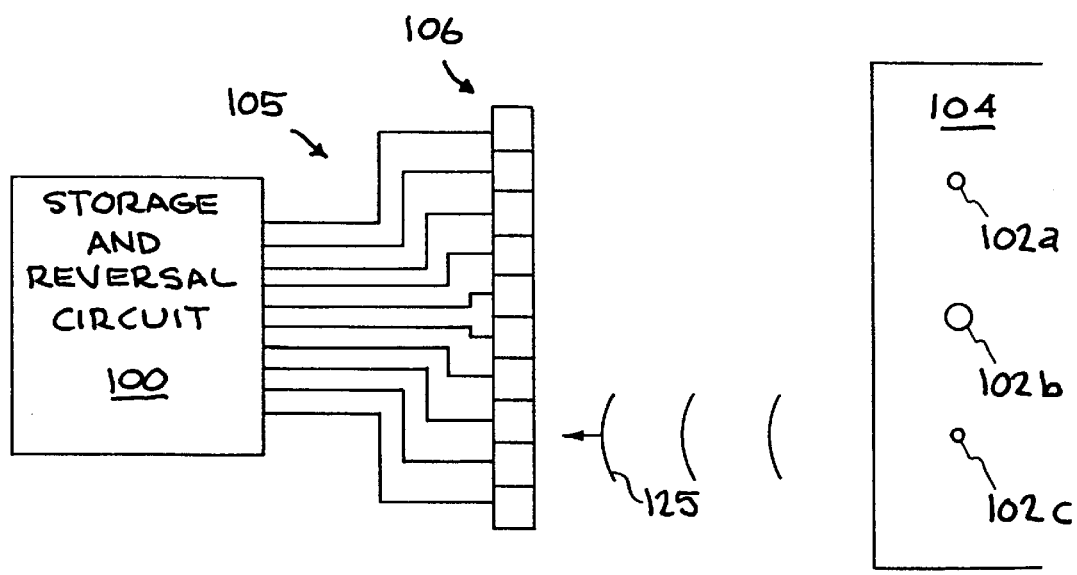

In operation, initially an unfocused beam 107 will be sent toward the scatterers 102a–102c from the transceiver elements of array 106. The scatterers 102a–102c will constitute secondary sources due to reflection (or echoes) from their surfaces. FIG. 1B discloses the next step of the process whereby reflections 108, 109 and 110 from scatterers 102a–102c are received by the transceiver elements of the array 106 and transformed into electrical signals traveling on connectors 105. The larger scatterer 102b returns a strong reflection 109 and the smaller scatterers 102a and 102c return weaker reflections 108 and 110 (shown in dotted lines to indicate weaker signals). The storage and reversal circuit 100 stores the shape and position in time (i.e., time series measurement data) of the electrical signals. During the next step, the time series measurement data is time-reversed (which will be discussed in detail below) and after several iterations, the strongest scatterer 102b is focused on, separated and removed from the time series measurement data. In a next step, array 106 transmits wavefronts 112 and 114 as shown in FIG. 1C. Wave fronts 112 and 114 illuminate other scatterers including 102a and 102c. FIG. 1D shows the newly reflected wave fronts 116 and 119. Reflected wavefront 116 is greater in strength than reflected wavefront 119 because scatterer 102a is larger in size than scatterer 102c and thus a greater reflector. Again, the data is time-reversed in the storage and reversal circuit 100 and after several iterations, focusing on scatterer 102a occurs and it is separated and removed from the time series measurement data. In a next step, array 106 transmits wavefront 122 as shown in FIG. 1E. FIG. 1F shows the reflected wavefront 125. Reflected wave front 125 from scatterer 102c is the strongest and scatterer 102c is identified as the third largest scatterer. Iterations of this process may be repeated a plurality of times and each time removing the scatters from the time series measurement data until a map of substantially all of the scatterers in the inhomogenous medium 104 is made. After identification of all of the scatterers in the medium 104 is made, the storage and reversal circuit 100 may concentrate ultrasound waves on the scatterers that are to be destroyed.

FIG. 2A illustrates a detailed version of storage and reversal circuit 100. Storage and reversal circuit 100 is designed to direct the focusing, detection, separation and destruction functions of the disclosed embodiments. Storage and reversal circuit 100 collects the time series measurement data from each transceiving element of the multisensor array 106 through a multiplexer system 202. The time series measurement data is then digitized in analog-to-digital (A/D–D/A) conversion amplifier 204 which may operate at ultrasonic frequencies (in the range of about 1 to about 10 MegaHertz (MHz)) and sent to a time-reversal system 206. FIG. 2B illustrates a view of time-reversal system 206. The time reversal system 206 is designed to perform the following functions: detect 208 whether the system has focused on the strongest scatterer; if so, then substantially remove 210 the strongest scatterer time series from the combined total time series measurement data; and if not, reorder in time (reverse) the time series for eventual transmission through conversion amplifier 204, multiplexer system 202, and array 106 into the medium 104. An example of the type of elements used in time-reversal system 206 may be found in U.S. Pat. No. 5,092,336 to Fink, hereby incorporated by reference.

Figure 3A:
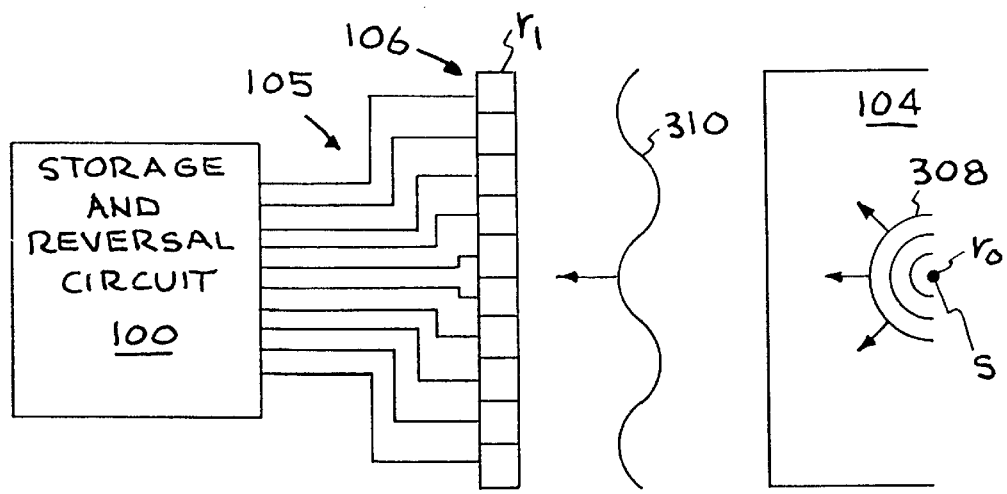
FIGS. 3A–3B illustrate a schematic diagram of a time-reversal focusing operation.
Figure 3B:
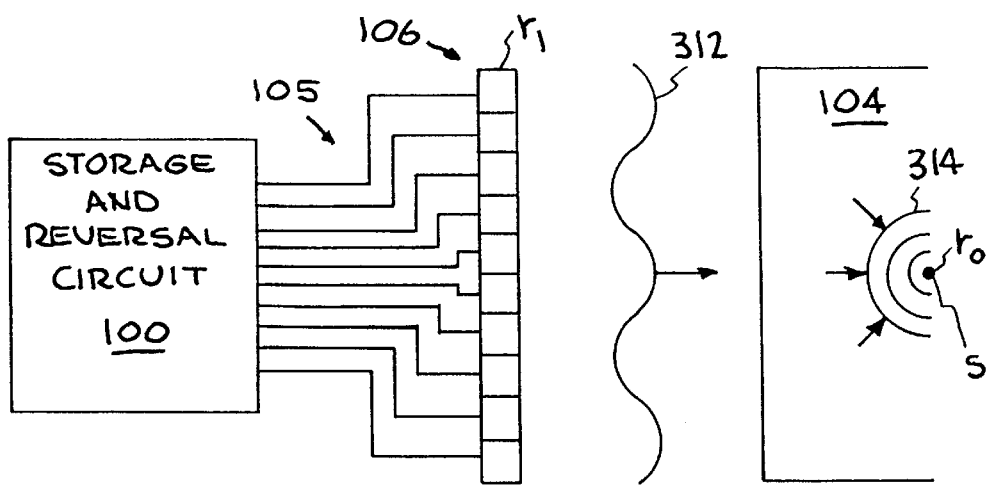

The processing steps that occur in the time reversal system 206 during operation may be characterized by the following discussion and referring to FIGS. 3A–3B. FIG. 3A illustrates a scatterer s which functions as a source in medium 104 located at position $r_0$. After receiving an initial pulse wave from array 106, reflected back from the source s at location $r_0$ and at time t is a spatio-temporal propagation (or wave), $s(r_0,t)$, or reflection 308. The reflection 308 travels back through the medium 104 and combines with other scatterer reflections to form a large combined reflection 310 which is sensed by array 106 which is located at $r_1$. The array 106 transforms the reflection 310 into electrical signals (which represent the time series measurement data) which is passed to the storage and reversal circuit 100 over connectors 105. The storage and reversal circuit 100 is designed to perform the scatterer response measurement which is the convolution of the Green's function, $G(r, r_0;t)$, with the scatterer s at location $r_0$ to location $r_1$ at array 106. Green's Function is an integrating kernal which may be used to solve an inhomogeneous differential equation with boundary conditions or more simply the response of the medium, both spatially and temporally, when an impulse-like excitation is propagated into the medium (medium impulse response). This operation is given by the following convolution operation to yield the received signal, R(r,t). (Convolution is a method of analyzing the response of a linear system to any input function). In this case, $$R(r_i, t) = G(r, r_o; t) * s(r_o, t) \overset{F}{\Longleftrightarrow} R(r, \omega) = G(r, r_o; \omega) S(r_o, \omega),$$

where $R(r_1,t)$ is the combined total field received on each sensor of array 106, $G(r,r_0;t)$ is the Green's function and $s(r_0,t)$ is the wave of the source and $R(r,\omega)$, $G(r, r_0;\omega)$ and $s(r_0, \omega)$ show the equivalent Fourier transform representations. In the next step as illustrated by FIG. 3B, based on this underlying theory, there will be a "re-transmit" from array 106 at $r_1$ through the medium 104 back to the original source position at $r_0$. Depending on whether the goal is to focus on the source, s, or to not "see" the source in the time series measurement data, the shape and strength of the transmitted wave will be determined. Time-reversed signal, R(r,−t), may be transmitted from storage and reversal circuit 100 through array 106 and into the medium 104 through wavefront 312 to source s at $r_0$ and the result is the focused signal 314:

$$\hat{s}(r_o, t) = G(r_o, r; t) * R(r, -t) \overset{F}{\Longleftrightarrow} \hat{S}(r_o, \omega) = G(r_o, r; \omega) R^*(r, \omega),$$

utilizing the Fourier transform conjugation property. By substituting the reversed signal and invoking the Reciprocity Theorem ($G(r_0, r,t) \equiv G(r,r_0;t)$) interchanging source and receiver position, the following is obtained:

$$\hat{s}(r_o, t) =$$

$$G(r_o, r; t) * G(r_o, r, -t) * s(r_o, -t) \overset{F}{\Longleftrightarrow} \hat{S}(r, \omega) = |G(r, r_o; \omega)|^2 S^*(r_o, \omega),$$

which implies that the reversed signals re-transmitted through the medium will "focus" the enhanced energy (with gain K) back to the original source position $r_0$ with no change in phase because of the magnitude-squared Green's function, that is, $$\hat{S}(r_0,\omega) K\, S(r_0,\omega),$$

which demonstrates the broadband version of phase conjugation. More sophisticated methods may be used which include sensor transfer functions, noise, etc., but the underlying time-reversal principle remains invariant—the phase has not been altered and the reversed signal re-focuses back to the original source location $r_0$.

As previously discussed, a feature of standard time-reversal operations is that in the multiple pitch/reverse/catch iterations—the strongest scatterer survives while the weaker attenuate out. The method and system of the embodiments disclosed herein, in constrast, include a time domain process to decompose the scattered field into its constituent sources/scatterers, even when they overlap, using the property of time-reversal processing and the removal process discussed below. The process disclosed herein systematically focuses on each individual scatterer and selectively removes it from the time series measurement data, thereby, providing detection and separation. Therefore, information about each individual scatterer is gathered from the decomposition process, potentially replacing the target under investigation with a sensor array 106 providing an accurate one-to-one part positional mapping. Next by re-transmitting the individually separated and reversed scatterer signals back to the sensor array, the target scatterer locations may be focused in the medium.

Thus a problem that is attacked with the process described herein is the decomposition of the field into a set of independent scatterer fields from noisy measurements. In the scatterer removal process, an image for this description (the technique is applicable to three-dimensional volumes as well) is started with the received pulse-echo field containing all of the scatterers given by R(r,t) (received combined total field at the array) where (in the two-dimensional case), $R \in C^{L \times N}$, where L is the number 20 of sensors in the array and N corresponds to the number of points in the temporal window to assure that the entire scattered response is captured (at least until the transients die out). $X_i(r,t)$ is the field generated by an individual scatterer (the i-th) propagated through the medium and becomes part of the combined total received field; therefore, it is a "stack" of the time series generated by the i-th scatterer and indexed by each sensor in the array. Through superposition, the total received field is given by the following equation:

$$R(r, t) = \sum_{i=1}^{N_S} \gamma_i \hat{X}_i(r, t)$$

where $\gamma_i$ is an unknown weighting coefficient which will be required to "scale" intermediate scattered fields. If it is assumed that the measured field is noisy, then the noisy combined total field is given by the following equation:

$$F(r,t) = R(r,t) + N(r,t)$$

where N is the spatio-temporal random (white) sensor or measurement noise generated by the inherent electronics and small scatterers that contaminate each of the time samples. Thus, using this scattering model the total residual or difference between the noisy combined total field (measured) and the reconstructed or estimated combined total received field is defined with all scatterers removed by $$\epsilon(r,t) = F(r,t) - \hat{R}(r,t),$$

where $\hat{R}(r,t)$ is the reconstructed combined total received field composed of weighted individual scattered fields reconstructed from estimates (time-reversal) of each of the strongest scatterers, $\{X_i(r,t)\}$, $i=1, \ldots, N_s$ and therefore $$\hat{R}(r, t) = \sum_{i=1}^{N_S} \gamma_i \hat{X}_i(r, t).$$

It may be seen that as the estimated field approaches the true (noise-field), $\hat{R} \rightarrow R$, then the residual should approach white noise, $\epsilon \rightarrow N$. The estimated field is decomposed into the individual "weighted" scatterer fields by first defining the reconstructed component (weighted) of the combined total received field generated by the i-th scatterer as $$\hat{R}_i(r,t) = \gamma_i \hat{X}_i(r,t),$$

then the reconstructed combined total received field becomes $$\hat{R}(r, t) = \sum_{i=1}^{N_S} \hat{R}_i(r, t).$$

Using this representation the corresponding "total" residual becomes $$\varepsilon(r, t) = F(r, t) - \sum_{i=1}^{N_s} \hat{R}_i(r, t).$$

By extracting the field generated by the first scatterer (first term in the summation) and defining the first residual as the difference between the noisy combined total received field and the reconstructed component of the combined total received field with one scatterer removed as $$\epsilon_1(r,t) \equiv F(r,t) - \hat{R}_1(r,t)$$

and continuing over all $N_s$ scatterers, the following recursion may be derived:

$$\epsilon_i(r,t) = \epsilon_{i-1}(r,t) - \hat{R}_i(r,t), i=1, \ldots, N_s$$

with $\epsilon_0(r,t) \equiv F(r,t)$, the original noisy combined total received field. Thus, it may seen that when the "last" scatterer is removed, $i = N_s$, then $$\epsilon(r,t) = \hat{\epsilon}_{N_s}(r,t) \rightarrow N(r,t),$$

that is, all of the scatterers have been removed from the original received field and what remains is the uncorrelated sensor noise. This is the decomposition condition which may be tested for statistical whiteness.

To complete the process, a technique is developed to estimate the set of unknown weighting coefficients, $\{\gamma_i\}, i=1, \ldots, N_s$. Each weighting coefficient may be sequentially estimated until there has been systematic removal of all of the scatterers from the measured field. In order to estimate the set of weighting functions, the following optimization problem is solved using the squared-residual error function at the i-th stage to be minimized, that is, at each stage there is found the coefficient to minimize the squared error performance function, J as $$\min_{\gamma_i} J_i = \hat{\varepsilon}_i^2(r, t)$$

based on the sequence of residual fields extracted in each time-reversal iteration. The Nelder-Meade polytope process may be used. This approach may be employed in conjunction with the time-reversal process.

The time-reversal scatterer decomposition process 400 is shown in FIG. 4. In a first step 402, the process includes obtaining the initial scattered, pulse-echo field (normalized to unit power), $\epsilon_0$ (r, t)≡F (r, t), where $\epsilon_0$ is the zero-th residual with no scatterers removed or more simply the noisy combined total received field. In a second step 404, the time-reversal iteration $\epsilon_{i-1}$(r,−t) is performed to extract the field contribution of the i-th scatterer, $X_i$(r, t) and normalize. In a third step 406, optimization is used to estimate the i-th weighting coefficient, $\gamma_i$, and obtain the corresponding reconstructed component of the combined total received field, $\hat{R}_i$(r,t). In a fourth step 408, the i-th residual (with i-scatterers removed), $\epsilon_i$(r,t), is estimated. In a fifth step 410, testing is performed to see if the decomposition condition (whiteness of residual) is satisfied. In a sixth step, if the fifth step is satisfied (i.e., all scatterers have been extracted from the measured field) then stop or else proceed back to the second step and remove the next scatterer.

An advantage of the disclosed embodiments is that they may be used in tissue mass removal, non-invasive tumor/cyst destruction, acoustic surgery, mass imaging, nondestructive evaluation of materials. An advantage of the disclosed embodiments is that the ultrasonic energy may be used to both detect, separate and destroy tissue masses (tumors, cysts, etc.) in breasts and other parts of the anatomy.

An advantage of the disclosed embodiments is that it may be possible to create a "tissue image map" of the breast itself when conducting a breast examination.

An advantage of the disclosed embodiments is that they may be used to detect and identify flaws for non-destructive evaluation (NDE) of critical parts under ultrasonic test.

The foregoing discussion is illustrative only and is not to be construed as limiting thereof. The invention is defined by the following claims, with equivalents of the claims to be included therein.

What is claimed is:

1. A method of decomposing a plurality of scatterers in a medium in the time domain comprising:
   a) transmitting a time reversed field into the plurality of scatterers of the medium and performing a sequence of time-reversal iterations to extract contribution of the i-th scatterer of the plurality of scatterers;
   b) estimating a weighting coefficient of the i-th scatterer of the plurality of scatterers;
   c) estimating the plurality of scatterers of the medium with the i-th scatterer removed;
   d) testing to see if a decomposition condition is satisfied; and
   e) performing a plurality of iterations of steps a through d until the decomposition condition is satisfied.

2. The method of claim 1, further including:
   obtaining an initial time series measurement data of the scattered field of the medium.

3. The method of claim 1, further comprising:
   f) reconstructing the medium to determine the number and size of the plurality of scatterers.

4. The method of claim 3, further comprising:
   g) destroying at least one of said plurality of scatterers.

5. A method to decompose a plurality of scatterers in a medium comprising:
   a) transmit a time reversed field into the plurality of scatterers of the medium and perform a sequence of time-reversal iterations to extract contribution of the i-th scatterer in order of descending size of the plurality of scatterers;
   b) estimate a weighting coefficient of the i-th scatterer of the plurality of scatterers;
   c) estimate the plurality of scatterers of the medium with the i-th scatterer removed;
   d) test to see if a decomposition condition is satisfied; and
   e) perform a plurality of iterations of steps a through d until the decomposition condition is satisfied.

6. The method of claim 5, wherein steps a through e are performed in the time domain.

7. A method of performing nondestructive evaluation (NDE) by decomposing a plurality of scatterers in a medium in the time domain comprising:
   a) transmit a time reversed field into the plurality of scatterers of the medium and perform a sequence of time-reversal iterations to extract contribution of the i-th scatterer of the plurality of scatterers;
   b) estimate a weighting coefficient of the i-th scatterer of the plurality of scatterers;
   c) estimate the plurality of scatterers of the medium with the i-th scatterer removed;
   d) test to see if a decomposition condition is satisfied; and
   e) perform a plurality of iterations of steps a through d until the decomposition condition is satisfied.

8. A method comprising steps of:
   illuminating a medium having a plurality of scatterers with an unfocused acoustic beam;
   receiving time series measurement data signals including shape and position information of each of said plurality of scatterers at an array of transceiving elements;
   storing the shapes and positions of the time series measurement data in a storage and reversal unit to form a total received field measurement;
   reversing the distribution in time and the shapes of each of the time series measurement data signals;
   applying each of said reversed time series measurement data signals to the transceiving elements of the array and transmitting said reversed time series measurement data signals to the medium; and
   sequentially removing each of the plurality of scatterers from the total received field measurement.

9. The method of claim 8, wherein said plurality of scatterers are sequentially removed from the total received field measurement in descending order by size and/or distance away from the array.

10. A system comprising:
    an array;
    a storage and reversal circuit connected to said array and designed to perform the following steps:
    a) transmit a time reversed field into a plurality of scatterers of a medium and perform a sequence of time-reversal iterations to extract contribution of the i-th scatterer of the plurality of scatterers;
    b) estimate a weighting coefficient of the i-th scatterer of the plurality of scatterers;
    c) estimate the plurality of scatterers of the medium with the i-th scatterer removed;
    d) test to see if a decomposition condition is satisfied; and
    e) perform a plurality of iterations of steps a through d until the decomposition condition is satisfied.

11. A system comprising:
    a means for transmitting a time reversed field into a plurality of scatterers of a medium and perform a sequence of time-reversal iterations to extract contribution of the i-th scatterer of the plurality of scatterers;

a means for estimating a weighting coefficient of the i-th scatterer of the plurality of scatterers;

a means for estimating the plurality of scatterers of the medium with the i-th scatterer removed;

a means for testing to see if a decomposition condition is satisfied; and a means for performing a plurality of iterations until the decomposition condition is satisfied.

12. A system comprising:

an array capable of transmitting an acoustic wave; and a storage and reversal circuit operatively coupled to said array and designed to receive time series measurement data of a plurality of scatterers in a medium and decompose the plurality of scatterers by systematically focusing on each of said plurality of scatterers and sequentially removing from the time series measurement data the largest of said plurality of scatterers.

13. The system of claim 12, wherein said storage and reversal circuit is designed to continue removing the plurality of scatterers from the time series measurement data until a decomposition condition is met.

14. The system of claim 13, wherein said decomposition condition is a white noise.

15. The system of claim 12, wherein said storage and reversal circuit is designed to continue removing the plurality of scatterers until the medium is mapped.

16. The system of claim 12, wherein said storage and reversal circuit is designed to focus on and destroy at least one of said plurality of scatterers.

17. The system of claim 12, wherein said storage and reversal circuit is designed to operate in the time domain.

18. A system comprising:

an array capable of transmitting an acoustic wave; and a storage and reversal circuit operatively coupled to said array and designed to receive time series measurement data of a plurality of scatterers in a medium and decompose the plurality of scatterers by systematically focusing on each of said plurality of scatterers and sequentially removing from the time series measurement data the plurality of scatterers.

19. The system of claim 18, wherein the plurality of scatterers are removed from the time series measurement data in order of size and/or distance away from the array.

20. The system of claim 18, wherein said storage and reversal circuit is designed to continue removing the plurality of scatterers from the time series measurement data until a decomposition condition is met.

* * * * *